United States Patent [19]

Kaufhold et al.

[11] 4,250,343

[45] Feb. 10, 1981

[54] PROCESS FOR THE PREPARATION OF PURE $\alpha,\omega$-$C_6$- TO $C_{20}$-ALKENOLS

[75] Inventors: Manfred Kaufhold, Marl; Werner Jacquemin, Haltern, both of Fed. Rep. of Germany

[73] Assignee: Chemische Werke Huls Aktiengesellschaft, Marl, Fed. Rep. of Germany

[21] Appl. No.: 117,322

[22] Filed: Jan. 31, 1980

[30] Foreign Application Priority Data

Feb. 7, 1979 [DE] Fed. Rep. of Germany ....... 2904518

[51] Int. Cl.³ .................... C07C 29/60; C07C 33/025
[52] U.S. Cl. ............................. 568/903; 260/346.11; 585/611
[58] Field of Search ......................................... 568/903

[56] References Cited

U.S. PATENT DOCUMENTS

| | | | |
|---|---|---|---|
| 2,086,713 | 7/1937 | Grun | 568/903 |
| 2,174,280 | 9/1939 | Wellman | 568/903 |
| 3,461,176 | 8/1969 | Lundeen et al. | 568/903 |
| 3,862,964 | 1/1975 | Weisang et al. | 568/903 |
| 3,893,946 | 7/1975 | Weisang et al. | 568/903 |
| 3,957,900 | 5/1976 | Weisang et al. | 568/903 |

FOREIGN PATENT DOCUMENTS 1355704 6/1974 United Kingdom .
156948 5/1962 U.S.S.R. .................................... 568/903

*Primary Examiner*—Joseph E. Evans
*Attorney, Agent, or Firm*—Millen & White

[57] ABSTRACT

A process for preparing an $\alpha,\omega$-$C_6$- to $C_{20}$-alkenol of a purity of greater than 85% comprises catalytically dehydrating the corresponding $\alpha,\omega$-$C_6$- to $C_{20}$-diol using a catalyst of a neutral, pyrophosphate of lithium, sodium, strontium or barium or a mixture thereof at a temperature of 300°–500° C. and a diol conversion of 10–90%.

7 Claims, No Drawings

PROCESS FOR THE PREPARATION OF PURE $\alpha,\omega$-$C_6$- TO $C_{20}$-ALKENOLS

BACKGROUND OF THE INVENTION

The present invention relates to a process for the preparation of $\alpha,\omega$-$C_6$- to $C_{20}$-alkenols of high purity by the catalytic dehydration of the corresponding $\alpha,\omega$-$C_6$- to $C_{20}$-diols.

The dehydration of alcohols is a conventional method, which is also utilized technically and industrially, to prepare olefins and/or generally to introduce a double bond into a molecule. (See, e.g., "Ullmanns Enzyklopaedie der technischen Chemi" [Ullmann's Encyclopedia of Technical Chemistry] 10 [1958]: 41 and 8 [1957]: 695 and 696.) It is furthermore known that such dehydrations can be conducted most easily with tertiary alcohols. The reaction is more difficult for secondary alcohols and can be effected only under extreme conditions with primary alcohols.

Moreover, in such dehydrations in the liquid as well as gaseous phases at temperatures above 350° C. in the presence of acidic catalysts and in the presence of solid catalysts, a shift of the position of the double bond occurs to a partial extent. With increasing reaction temperatures, this positional shift occurs to an increasing extent. If it is desired to produce uniform products free of isomers, the resultant positional isomers in the reaction product represents a grave problem. Therefore, various methods have been suggested to prevent isomerization. However, when interpreting the older treatises, it must be borne in mind that often the analytical methods available at the time of the writing frequently were not capable of the exact characterization of the reaction products. (See, e.g., Houben-Weyl, "Methoden der organischen Chemie" [Methods of Organic Chemistry] V/1b "Alkenes, Cycloalkenes, Arylalkenes" [1972]: 45 et seq.)

The actual extent of isomerization can only be determined by means of exact analytical methods, for example, by gas chromatographic analyses. Literature data which are not based on such accurate analytical methods cannot reliably indicate anything regarding the selectivity of the reaction. Since the isomerization is catalyzed by acids or by acidic centers on the solid catalysts, it occurs especially during the dehydration of primary alcohols requiring drastic conditions for the elimination of water, i.e., strong acids and high temperatures. All of the conventional processes for dehydrating alcohols while minimizing isomerization, thus, have as an objective the maximum avoidance of strong acids and relatively high reaction temperatures during the reaction, and of at least partially neutralizing the acidic centers with bases when using solid catalysts. Suitable bases for ameliorating the acidic character of a catalyst include, for example, nitrogen compounds, such as ammonia, tertiary amines, pyridines, etc., and also sodium hydroxide solution and sodium carbonate solution.

Such partial neutralization of solid catalysts, however, also entails grave disadvantages. Although the suppression of isomerization is more effective, the more basic is the compound employed to lessen acidity; concomitantly, the higher is the reduction in activity of the catalyst. The higher purity of the reaction product must, accordingly, be attained at a cost of long reaction periods. An additional disadvantage of these partially neutralized catalysts is the shorter resultant catalyst lifetime.

The dehydration of amyl alcohol in the presence of tricalcium phosphate at 440° C., for example, yields 86.9% of pentenes with a 1-pentene content of 20.2%. After treating the catalyst with sodium hydroxide solution, the 1-pentene content does rise to 97.2%, but the yield in pentenes decreases to 74.6%. Furthermore, the catalyst treated with sodium hydroxide solution must be are generated after only 100 hours, since its activity has been excessively reduced (Chem. Abstr. 58: 2353 [1963]). Such processes having catalyst operating periods of only a few days are uneconomical and thus are not implemented on an industrial scale.

All of the known processes, therefore, exhibit considerable disadvantages, in that they either result in nonuniform products using relating active catalysts at high space-time yields, or yield pure substances using partially neutralized catalysts in an uneconomical mode of operation.

SUMMARY OF THE INVENTION

Accordingly, it is an object of this invention to provide a method for the production of $\alpha,\omega$-$C_6$ to $C_{20}$-alkenols by the dehydration of $\alpha,\omega$-diols which operates at minimum technological and industrial expenditure, which uses catalysts having long lifetimes and which possesses such a high selectivity that it yields a low number of by-products and pure, i.e., at least 85% strength, $\alpha,\omega$-alkenols.

It is especially an object of this invention to provide a dehydration method for such difunctional compounds which fulfills the high demands regarding the selectivity of the position toward the production of such alkenols having the double bond in the $\alpha$-position.

Upon further study of the specification and appended claims, further objects and advantages of this invention will become apparent to those skilled in the art.

These objects have been attained by this invention by providing a process for preparing $\alpha,\omega$-$C_6$ to $C_{20}$-alkenols comprising dehydrating $\alpha,\omega$-$C_6$ to $C_{20}$-diols using neutral, simple or complex pyrophosphates of lithium, sodium, strontium or barium and/or mixtures of these compounds as catalysts, at temperatures of 300°–500° C., selectively and partially into pure $\alpha,\omega$-$C_6$ to $C_{20}$-alkenols having degrees of purity above 85%, determined, for example, by gas-chromatographic analysis, with attainment of a diol conversion of 10–90% being achieved by regulation of the residence time.

DETAILED DISCUSSION

Surprisingly, when dehydrating the $\alpha,\omega$-$C_6$ to $C_{20}$-diols, instead of the expected dienes, $\alpha,\omega$-$C_6$ to $C_{20}$-alkenols are obtained in good yields and in high degrees of purity.

Herein, the neutrality of the pyrophosphates refers to the catalyst as a whole; for even in the case of "neutral" catalysts there are still centers with weakly acidic properties (Houben-Weyl V/1b: 47 and 48). Whether or not an overall neutral catalyst possesses acidic centers can readily be ascertained from the nature of the reaction products, since the extent of isomerization is greater, the more acidic the catalyst is.

Neutral, simple or complex pyrophosphates of lithium, sodium, strontium or barium are known as dehydration catalysts from German Pat. No. 2,117,444, equivalent to British Pat. Nos. 1,355,704 and 1,355,705. The disclosures of these references are incorporated by reference herein, especially as regards the nature of the suitable pyrophosphate catalyst including the methods of preparation thereof.

It is emphasized in these references that these catalysts are suitable for the dehydration of vicinal diols having secondary hydroxy groups, whereas acidic catalysts are employed for dehydration of other diols having primary hydroxy groups. Surprisingly, however, it has been found that neutral, simple or complex pyrophosphates of lithium, sodium, strontium or barium, or mixtures of these compounds, are suitable catalysts for the selective and partial dehydration of $\alpha,\omega$-$C_6$ to $C_{20}$-diols to $\alpha,\omega$-$C_6$ to $C_{20}$-alkenols. Using these catalysts, at temperatures of 300°–500° C., preferably 380°–450° C., $\alpha,\omega$-$C_6$ to $C_{20}$-alkenols are obtained having a purity as determined, for example, by gas chromatography, of more than 85% and containing only 2–10% of isomerization products. Especially suitable is barium pyrophosphate, by means of which the $\alpha,\omega$-$C_6$ to $C_{20}$-alkenols are obtained in a purity of more than 92%.

It can clearly be seen from Example II of German Pat. No. 2,117,444 (=British Pat. No. 1,355,704, Example 2), wherein the alcohol content of the reaction product is higher than in the other examples, that isomerization has taken place to a high degree. That is, 76% of 2-methyl-1-butenol-(3) is present in comparison with 14.4% of isomerization products, for example 3-methyl-2-butenol-(1) formed by allylic rearrangement. Example V of this patent demonstrates that the isomerization greatly increases when the temperature is elevated from 400° to 500° C. On the basis of these data, it can only be assumed that $\alpha,\omega$-$C_6$ to $C_{20}$-diols would yield at least just as many isomerization products as the vicinal diols.

Furthermore, since primary hydroxy groups cannot be eliminated as readily as secondary hydroxy groups, the need for higher temperatures would be anticipated for the use of the neutral pyrophosphates in this invention. These higher temperatures, of course, would be expected to significantly lower the selectivity of the reaction. Surprisingly, however, it has been found that, in spite of the high temperatures employed, the reaction of this invention proceeds in a much more selective fashion than the prior art dehydration of secondary alcohols described in the examples of Ger. Pat. No. 2,117,444 (=British Pat. No. 1,355,704).

The neutral, pyrophosphates suitable as catalysts for this invention exhibit high activities which are retained even after operating periods of more than one month. Such lifetimes are unattainable using partially neutralized catalysts.

In contradistinction to the process of German Pat. No. 2,117,444 (=British Pat. No. 1,355,704), the process of the present invention operates with conversions of less than 100%, namely 10–90%, preferably 40–80%. Surprisingly high yields of $\alpha,\omega$-$C_6$ to $C_{20}$-alkenols of 50–90% are obtained in this range, with a very low attendant formation of undesired diene byproduct, e.g., concentrations thereof of only about 0.5–2% in the reaction product. A conversion of diol of 40–80% is preferred, since the economy and efficiency of the process is high in this range due to high space-time yields. With conversion rates of above 80%, byproduct diene formation gradually increases, and with conversion rates of more than 90%, byproduct diene formation is greatly elevated.

The determination and control of the conversion rate may be accomplished by fully conventional methods. For example, the conversion rate can be determined by gas chromatography, optionally in a preliminary experiment. In order to control the conversion rate, the residence time and/or temperature can be adjusted in dependence on the thus-determined conversions.

Unless otherwise indicated herein, all conditions for carrying out the dehydration of this invention are fully conventional and can be determined by the customary considerations employing, e.g., routine experiments, by one of ordinary skill in the art. For example, see the above-mentioned references relating to dehydration reactions.

For example, in general, the process of this invention can be carried out in any suitable conventional reactor, e.g., the amount of catalyst employed is not critical. For example, an amount of catalyst of 50–85 volume percent based upon the volume of the reactor can be employed. Also, suitable flow rates of the starting material diol can vary over a wide range, e.g., 200–600 g/hour for reactors of a volume of 1 liter. It is preferred that the reaction be conducted in an inert atmosphere such as nitrogen, argon, etc. For a continuous reaction, the gas used as the inert atmosphere may be continuously added, e.g., at a rate of 50–300 Nl/h for reactors of the mentioned volume. Generally, the reaction proceeds at pressures of 0.1–5 atmosphere, preferred 1–2 atmosphere.

Under the mentioned exemplary conditions, residence times typically are 150–400 minutes related to the free volume of the reactor, for the attainment of the conversions required by this invention. Although the process of this invention is described primarily in terms of a continuous operation, batch operation is also feasible using the correspondingly appropriate conditions.

The high yields of $\alpha,\omega$-$C_6$ to $C_{20}$-alkenols obtained by dehydration of $\alpha,\omega$-$C_6$ to $C_{20}$-diols per this invention are particularly surprising inasmuch as $\alpha,\omega$-diols can undergo numerous secondary reactions. These include the ready formation of cyclic ethers and high-molecular weight polyethers. For example, using these same dehydration catalysts, 1,4-butanediol yields almost exclusively tetrahydrofuran (see Comparative Example 1); and, 1,5-pentanediol yields a high proportion of tetrahydropyran (see Comparative Example 2).

The $\alpha,\omega$-alkenols of 6–20 carbon atoms obtained according to the process of this invention are valuable intermediates for numerous other technical and industrial syntheses, e.g., for the preparation of herbicides and insecticides as hexantriol-1,2,6 and for the preparation of scents as undecen-1-al-11.

Without further elaboration, it is believed that one skilled in the art can, using the preceding description, utilize the present invention to ist fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

COMPARATIVE EXAMPLE 1

A quartz tube, 30×500 mm, with an electrical heating jacket, is filled with 250 ml of barium pyrophosphate, prepared according to the details of Example 2 of German Pat. No. 2,117,444, (British Pat. No. 1,355,704, Example 3). At a contact temperature of 380° C., 87 g/h of 1,4-butanediol is introduced dropwise on the catalyst from a dropping funnel. At the same time, 23 Nl/h of nitrogen is fed to the head of the catalyst tube. The conversion of 1,4-butanediol is 74%, the yield in tetrahydrofuran is 72% of theory, and in butene-1-ol, 3% of theory. The discharge from the furnace, amounting to 237 g, is distilled on a 25×200 mm multifil column with water trap, thus obtaining the following fractions:

| Fraction No. | B.P. (°C.) | Pressure (mbar) | Amount (g) |
|---|---|---|---|
| Cooling trap | | | 31 |
| 1 | 63–70 | 1,010 | 111 Tetrahydrofuran |
| 2 | 70–130 | 1,010 | 45 40 g H₂O, 5 g Butenols |
| 3 | 132–133 | 24 | 67 Unreacted Butanediol |
| Residue | | | 14 |

COMPARATIVE EXAMPLE 2

The quartz tube described in COMPARATIVE EXAMPLE 1 is utilized with the same catalyst charge. At a contact temperature of 430° C., 173 g/h of 1,5-pentanediol is added dropwise onto the catalyst from a dropping funnel. At the same time, 45 Nl/h of nitrogen is introduced to the head of the catalyst tube. The single-phase discharge from the furnace, amounting to 415 g, is distilled on a 25×500 mm multifil column with water trap. The following fractions are obtained:

| Fraction No. | B.P. (°C.) | Pressure (mbar) | Amount (g) |
|---|---|---|---|
| 1 | 75 | 1,010 | 70 H₂O/Oil Azeotrope |
| 2 | 80–100 | 1,010 | 96 Tetrahydropyran |
| 3 | 50–70 | 26 | 107 Pentenols |
| 4 | 70–145 | 26 | 109 Unreacted Pentanediol |
| Residue | | | 27 |

Fraction 3, according to analysis by gas chromatography, consists of 92.1% of penten-1-ol-5. The result of the distillation shows that, besides the dehydration to pentenols, a cyclizing dehydration to tetrahydropyran takes place to almost the same extent.

The 1,5-pentanediol conversion is 79%, the pentenol yield is 32% of theory and the tetrahydropyran yield is 28% of theory.

EXAMPLE 1

In the apparatus described in COMPARATIVE EXAMPLE 1 with the same catalyst charge, 87 g/h of 1,6-hexanediol is dripped onto the catalyst from a dropping funnel at a contact temperature of 410° C. At the same time, 23 Nl/h of nitrogen is fed to the head of the catalyst tube. The conversion, determined by gas chromatography, is 65%.

The discharge from the furnace, amounting to 245 g, is distilled on a 25×500 mm multifil column with water trap, thus obtaining the following fractions:

| Fraction No. | B.P. (°C.) | Pressure (mbar) | Amount (g) |
|---|---|---|---|
| Cooling trap | | 13 | 29 H₂O |
| Cooling trap | | 13 | 25 Hexadiene |
| 1 | 64–65 | 13 | 98 Hexenols |
| 2 | 135–142 | 13 | 91 Unreacted Hexanediol |
| Residue | | | 3 |

Fraction 1 was analyzed by gas chromatography.

| | |
|---|---|
| Forerunnings | 0.9% by weight |
| Hexanol | 1.8% by weight |
| Hexen-1-ol-6 | 92.5% by weight |
| trans-Hexen-2-ol-6 | 1.7% by weight |
| cis-Hexen-2-ol-6 | 0.8% by weight |
| Remainder | 2.3% by weight |

The conversion of 1,6-hexanediol is 65%; the yield is hexen-1-ol-6 (calculated on 100% conversion of starting material) is 62.2% of theory.

EXAMPLE 2

A 650 ml V2A stainless steel furnace with an electrical heating jacket is charged with 600 ml of barium pyrophosphate. At a contact temperature of 430° C., 180 g/h of 1,10-decanediol is added dropwise to the head of the furnace. At the same time, 60 Nl/h of nitrogen is passed through the furnace. The conversion as determined by gas chromatography is 68%.

The discharge from the furnace is then distilled, thus obtaining the following fractions:

| | |
|---|---|
| Water | 7.2% by weight |
| Decadiene | 6.0% by weight |
| Decenols | 47.6% by weight |
| Unreacted Decanediol | 32.6% by weight |
| Residue | 6.5% by weight |

The analysis of the decenol fraction by gas chromatography yields the following:

| | |
|---|---|
| Forerunnings | 0.25% by weight |
| Decanol | 3.0% by weight |
| Decen-1-ol-10 | 95.1% by weight |
| trans-Decen-2-ol-10 | 0.7% by weight |
| cis-Decen-2-ol-10 | 0.2% by weight |
| Remainder | 0.75% by weight |

The decanediol conversion is 68%; the yield in decen-1-ol-10 (calculated: 100%) is 69.4% of theory.

After an operating period of 30 days, the catalyst still exhibits the same activity and selectivity.

EXAMPLE 3

In accordance with the descriptions of COMPARATIVE EXAMPLES 1 and 2 and of EXAMPLE 1, 85 g/h of 1,12-dodecanediol and 23 Nl/h of nitrogen are passed through the furnace at a contact temperature of 425° C. The conversion as determined by gas chromatography is 67%. The fractionation of the discharge from the furnace yields the following:

| | |
|---|---|
| Dodecadienes | 13.9% |
| Dodecenols (b.p. 24 mbar 145°–149° C. | 49.1% |
| Unreacted Dodecanediol | 22.4% |
| Residue | 4.6% |

Analysis of the dodecenol fraction by gas chromatography yields the following:

| | |
|---|---|
| Forerunnings | 0.5% by weight |
| Dodecanol | 4.2% by weight |
| Dodecen-1-ol-12 | 92.2% by weight |
| trans-Dodecen-2-ol-12 | 1.8% by weight |

| | |
|---|---|
| cis-Dodecen-2-ol-12 | 0.5% by weight |
| Remainder | 0.6% by weight |

The conversion of 1,12-dodecanediol is 73%; the yield in dodecen-1-ol-12 (calculated: 100%) is 50% of theory.

EXAMPLE 4

Dehydration of 1,14-Tetradecanediol
Apparatus: as in COMPARATIVE EXAMPLE 1
Catalyst charge: as in COMPARATIVE EXAMPLE 1

The feed was from a heated dropping funnel into the head of the catalyst tube.

At a contact temperature of 410° C., 120 g/h of 1,14-tetradecanediol and 40 Nl/h of nitrogen are passed through the furnace.

The discharge from the furnace is distilled on a 25×200 mm, multifil column. The amount introduced into the distillation stage is 420 g. The fractionation of the discharge from the furnace has the following results:

| | |
|---|---|
| Tetradecadienes | 14.2% |
| Tetradecenol | 46.7% |
| Unreacted Tetradecanediol | 29.8% |
| Residue | 9.3% |

Analysis of the tetradecenol fraction by gas chromatography:

| | |
|---|---|
| Forerunnings | 0.4% by weight |
| Tetradecanol | 3.9% by weight |
| Tetradecen-1-ol-14 | 92.4% by weight |
| trans-Tetradecen-2-ol-14 | 1.9% by weight |
| cis-Tetradecen-2-ol-14 | 0.8% by weight |
| Remainder | 0.6% by weight |

The tetradecanediol conversion amounts to 70%; the yield in tetradecen-1-ol-14 (calculated: 100%) is 66% of theory.

EXAMPLE 5

Dehydration of 1,20-Eiconsanediol
Apparatus: as in EXAMPLE 4
Catalyst: as in EXAMPLE 4

At a contact temperature of 430° C., 95 g/h of 1,20-eicosanediol and 35 Nl/h of nitrogen are passed through the furnace.

The fractionation of the furnace discharge yields the following:

| | |
|---|---|
| Eicosadienes | 12.3% |
| Eicosenol | 48.7% |
| Unreacted Eicosandediol | 24.9% |
| Residue | 14.1% |

Analysis of the eicosenol fraction by gas chromatography:

| | |
|---|---|
| Forerunnings | 0.5% |
| Eicosanol | 3.9% |
| Eicosen-1-ol-20 | 93.1% |
| trans-Eicosen-2-ol-20 | 1.4% |
| cis-Eicosen-2-ol-20 | 0.7% |
| Remainder | 0.4% |

The eicosanediol conversion is 75%; the yield in eicosen-1-ol-20 (calculated: 100%) is 64% of theory.

EXAMPLE 6

The quartz tube as described in comparative Example 1, is used. This tube is filled with 250 ml of lithium pyrophosphate, prepared according to the directions in German Pat. No. 2,117,444, Example 3 (=British Pat. No. 1,355,704, Example 3). At a contact temperature of 450° C., 87 g/h of 1,10-decanediol is dripped through a dropping funnel onto the catalyst. At the same time, 23 Nl/h of nitrogen is introduced to the head of the catalyst tube. The conversion of 1,10-decanediol amounts to 59%; the yield in decenols is 71% of theory.

In accordance with analysis by gas chromatography, the distilled decenol has the following composition:

| | |
|---|---|
| 1-Decanol | 2.2% |
| Decen-1-ol-10 | 86.9% |
| trans-Decen-2-ol-10 | 4.8% |
| cis-Decen-2-ol-10 | 3.4% |
| High-Boiling Compounds | 1.1% |
| Residual Compounds | 1.6% |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing an $\alpha,\omega$-$C_6$- to -$C_{20}$-alkenol of a purity of greater than 85% comprising catalytically dehydrating the corresponding $\alpha,\omega$-$C_6$- to -$C_{20}$-diol using a catalyst of a neutral pyrophosphate of lithium, sodium, strontium or barium or a mixture thereof at a temperature of 300°–500° and a diol conversion of 10–90%.

2. The process of claim 1 wherein barium pyrophosphate is the catalyst.

3. The process of claim 1 wherein the conversion is controlled by regulating the residence time of the diol in the reaction.

4. The process of claim 1 wherein the pyrophosphate catalyst is a complex pyrophosphate.

5. The process of claim 1 wherein the pyrophosphate catalyst is a simple pyrophosphate.

6. The process of claim 1 wherein the temperature is 380°–450° C.

7. The process of claim 1 wherein the diol conversion is 40–80%.

* * * * *